US012773099B2

(12) United States Patent
Yi et al.

(10) Patent No.: US 12,773,099 B2
(45) Date of Patent: Oct. 27, 2026

(54) ENDOSCOPE KNOB BRAKE DEVICE, ENDOSCOPE HANDLE AND ENDOSCOPE

(71) Applicant: GUANGZHOU RED PINE MEDICAL INSTRUMENT CO., LTD., Guangzhou (CN)

(72) Inventors: Feng Yi, Guangzhou (CN); Jing Li, Beijing (CN); Xiaofeng Tan, Guangzhou (CN)

(73) Assignee: GUANGZHOU RED PINE MEDICAL INSTRUMENT CO., LTD., Guangzhou (CN)

( * ) Notice: Subject to any disclaimer, the term of this patent is extended or adjusted under 35 U.S.C. 154(b) by 264 days.

(21) Appl. No.: 18/575,192

(22) PCT Filed: Dec. 2, 2022

(86) PCT No.: PCT/CN2022/136192

§ 371 (c)(1),
(2) Date: Dec. 28, 2023

(87) PCT Pub. No.: WO2023/103905

PCT Pub. Date: Jun. 15, 2023

(65) Prior Publication Data

US 2024/0293007 A1 Sep. 5, 2024

(30) Foreign Application Priority Data

Dec. 7, 2021 (CN) ......................... 202111488259.1

(51) Int. Cl.
*A61B 1/005* (2006.01)
*A61B 1/00* (2006.01)

(52) U.S. Cl.
CPC ........ *A61B 1/0052* (2013.01); *A61B 1/00066* (2013.01); *A61B 1/0051* (2013.01); *A61B 1/0057* (2013.01)

(58) Field of Classification Search
CPC ............ A61B 1/00064; A61B 1/00066; A61B 1/00068; A61B 1/0051; A61B 1/0052;
(Continued)

(56) References Cited

U.S. PATENT DOCUMENTS

2003/0187328 A1 10/2003 Seki et al.
2009/0287188 A1 11/2009 Golden et al.
(Continued)

FOREIGN PATENT DOCUMENTS

CN 107485360 A 12/2017
CN 110301881 A 10/2019
(Continued)

OTHER PUBLICATIONS

International Search Report and Written Opinion (with English translation) received in corresponding Application No. PCT/CN2022/136192, dated Feb. 28, 2023, 14 pages.
(Continued)

*Primary Examiner* — Ryan N Henderson
(74) *Attorney, Agent, or Firm* — Dority & Manning, PA

(57) ABSTRACT

Disclosed are an endoscope knob brake device, an endoscope handle, and an endoscope. The endoscope knob brake device includes a fixed frame, brake members and a brake knob. The fixed frame includes an operating cavity configured for a knob mechanism to pass through. At least two sliding grooves are arranged at intervals around the operating cavity. The brake members are slidably installed in the sliding grooves in a one-to-one correspondence. The brake knob is sleeved over the fixed frame. At least two pushing portions are disposed at intervals on an inner wall of the brake knob. When the brake knob is rotated to a preset angle, the pushing portions push, in a one-to-one correspondence, the brake members to move toward the operating cavity to hold the knob mechanism tightly.

14 Claims, 9 Drawing Sheets

(58) Field of Classification Search
CPC ................ A61B 1/0055; A61B 1/0057; A61B 2017/00318; A61B 2017/00323; A61B 2017/00327; A61M 25/0136; A61M 25/0147
See application file for complete search history.

(56) References Cited

U.S. PATENT DOCUMENTS

| | | | | |
|---|---|---|---|---|
| 2015/0359415 | A1* | 12/2015 | Lang ................. | A61M 25/0147 600/141 |
| 2018/0049623 | A1 | 2/2018 | Golden et al. | |
| 2021/0007582 | A1 | 1/2021 | Graveley et al. | |

FOREIGN PATENT DOCUMENTS

| | | | | |
|---|---|---|---|---|
| CN | 209899331 | U | | 1/2020 |
| CN | 210871449 | U | | 6/2020 |
| CN | 210902905 | U | * | 7/2020 |
| CN | 210902906 | U | | 7/2020 |
| CN | 111528769 | A | | 8/2020 |
| CN | 114176487 | A | | 3/2022 |
| CN | 114403777 | A | | 4/2022 |
| CN | 217040072 | U | | 7/2022 |
| CN | 217040076 | U | | 7/2022 |
| JP | 2000217777 | A | | 8/2000 |
| JP | 2004313806 | A | | 11/2004 |
| JP | 2011182981 | A | | 9/2011 |
| JP | 2012249862 | A | | 12/2012 |

OTHER PUBLICATIONS

European Search Report received in corresponding Application No. 22903327.9, dated Apr. 22, 2025, 10 pages.

Chinese Office Action for corresponding Application No. 202111488259.1, dated Jul. 24, 2024, 10 pages.

Japanese Office Action (w/English translation) for corresponding Application No. 2023-581024, Oct. 29, 2024, 8 pages.

* cited by examiner

ENDOSCOPE KNOB BRAKE DEVICE, ENDOSCOPE HANDLE AND ENDOSCOPE

CROSS-REFERENCE TO RELATED APPLICATIONS

This application is a national stage application of PCT international application No. PCT/CN2022/136192 filed on Dec. 2, 2022, which claims priority to Chinese patent application No. 202111488259.1 filed with the Chinese Patent Office on Dec. 7, 2021, entitled "ENDOSCOPE KNOB BRAKE DEVICE, ENDOSCOPE HANDLE, AND ENDOSCOPE", the entire contents of which are incorporated by reference.

TECHNICAL FIELD

The present application relates to the technical field of medical devices, and particularly to an endoscope knob brake device, an endoscope handle, and an endoscope.

BACKGROUND

Endoscopes are inspection instruments that integrate traditional optics, ergonomics, precision machinery, modern electronics, mathematics, software, etc. It includes image sensors, optical lenses, light sources, mechanical devices, etc. As an important auxiliary medical instrument for examining lesions in the internal organs of the human body, the endoscope is widely used in various surgical operations. At present, most endoscope products are reusable and require strict disinfection after each use. A traditional endoscope includes a handle, an insertion tube, a bending section, a distal tip, and a host. The handle is integrated with structures such as functional buttons, air and water valves, negative pressure valves, three-way valves, etc.

In order to expand the observation range, the bending section is controlled to bend in four directions through a knob device, enabling the endoscope to observe in four directions.

SUMMARY

An endoscope knob brake device includes: a fixed frame defining an operating cavity configured for a knob mechanism to pass through, the fixed frame including at least two sliding grooves arranged at intervals around the operating cavity, one end of each sliding groove being in communication with the operating cavity, and the other end of each sliding groove being configured to communicate with an outside of the fixed frame; at least two brake members slidably installed in the sliding grooves in a one-to-one correspondence, each brake member passing through the sliding groove and extends out of the fixed frame; and a brake knob sleeved over the fixed frame. At least two pushing portions are disposed at intervals on an inner wall of the brake knob. When the brake knob is rotated to a preset angle, the pushing portions push, in a one-to-one correspondence, the brake members to move toward the operating cavity, thereby holding the knob mechanism.

In one of the embodiments, each sliding groove includes a first groove section, a second groove section, and a third groove section that are communicated in sequence. The first groove section is communicated with the operating cavity. The third groove section is configured to communicate with the outside of the fixed frame. The brake member is slidably installed in the second groove section. One end of the brake member extends into the first groove section, and the other end of the brake member passes through the third groove section and extends out of the fixed frame.

In one of the embodiments, each brake member includes a main body, a holding portion, and a transmission portion. The holding portion and the transmission portion are respectively arranged at opposite ends of the main body. The holding portion is located in the first groove section. The transmission portion is located in the third groove section and partially extends out of the fixed frame. Limiting walls are formed between the first groove section and the second groove section, and between the second groove section and the third groove section, respectively. The main body is slidably installed in the second groove section and is limited by the limiting wall between the first groove section and the second groove and the limiting wall between the second groove section and the third groove section.

In one of the embodiments, a width $W_1$ of the first groove section and a width $W_3$ of the third groove section are both smaller than a width $W_2$ of the second groove section, such that the limiting walls are formed between the first groove section and the second groove section, and between the third groove section and the second groove section, respectively. A width $W_4$ of the holding portion and a width $W_6$ of the transmission portion are both smaller than a width $W_5$ of the main body.

In one of the embodiments, the brake knob includes a knob body and an annular sleeve arranged on the knob body. The annular sleeve is sleeved over the fixed frame, and the pushing portions are arranged on an inner wall of the annular sleeve.

In one of the embodiments, the pushing portions are formed by the inner wall of the annular sleeve protruding toward a center of the annular sleeve.

In one of the embodiments, the brake knob includes an toggle portion protruding and extending along a radial direction of the brake knob. Alternatively, the brake knob includes an toggle portion protruding and extending in a direction away from the fixed frame.

In one of the embodiments, the fixed frame includes a first positioning portion configured to positionally cooperate with a second positioning portion on the knob mechanism to limit the fixed frame, such that the fixed frame rotates with the knob mechanism.

In one of the embodiments, the first positioning portion is a positioning groove or a positioning protrusion on the fixed frame.

In one of the embodiments, there are a plurality of first positioning portions, and the plurality of first positioning portions are arranged at intervals around the operating cavity.

In one of the embodiments, the brake knob includes arc-shaped grooves arranged around the operating cavity. The arc-shaped grooves are configured to cooperate with limiting columns on a housing of the knob mechanism to limit a rotation range of the brake knob. Alternatively, a first limiting block is disposed on an inner wall of the brake knob. Second limiting blocks are disposed on an outer wall of the fixed frame. The first limiting block cooperates with the second limiting blocks to limit the rotation range of the brake knob.

In one of the embodiments, an anti-skid structure is disposed at an end of each brake member facing the operating cavity.

In one of the embodiments, an end of each brake member facing the operating cavity fits an outer contour of the knob mechanism.

In one of the embodiments, the transmission portion, the main body, and the holding portion are integrated.

An endoscope handle includes a knob mechanism and two endoscope knob brake devices as described in any one of the above embodiments. The knob device includes a housing, a first cable pulley, a second cable pulley, a first knob, and a second knob. The first cable pulley extends out of the housing and is connected to the first knob. The second cable pulley passes through the first cable pulley, extends out of the housing, and is connected to the second knob. One of the endoscope knob brake devices is configured to brake the first knob or the first cable pulley, and the other one of the endoscope knob brake devices is configured to brake the second knob or the second cable pulley.

An endoscope including the above-mentioned endoscope handle is also provided.

BRIEF DESCRIPTION OF THE DRAWINGS

The accompanying drawings forming a part of the disclosure are used to provide a further understanding of the present disclosure. The illustrative embodiments of the present disclosure and descriptions thereof are used to explain the present disclosure and do not constitute an improper limitation of the present disclosure.

In order to illustrate the technical solutions of the embodiments of the present application more clear, the accompanying drawings used in the description of the embodiments will be briefly introduced below. It is apparent that the accompanying drawings described herein are only some embodiments of the present application. For those of ordinary skill in the art, other drawings can also be obtained from these drawings without creative efforts.

DETAILED DESCRIPTION OF THE EMBODIMENTS

In order to make the above purposes, features and advantages of the present disclosure more obvious and understandable, specific embodiments of the present disclosure will be described in detail below with reference to the accompanying drawings. Some specific details are set forth in the following description in order to facilitate a thorough understanding of the present disclosure. However, the present disclosure can be implemented in many other ways different from those described herein. Those skilled in the art can make similar improvements without departing from the connotation of the present disclosure. Therefore, the present disclosure is not limited to the specific embodiments disclosed below.

In order to expand the observation range of an endoscope, the bending section is controlled to bend in four directions through a knob device, enabling the endoscope to observe in four directions. When image information on a specific orientation is to be acquired, a knob device is locked by a braking assembly to maintain the bending section at a specific bending angle. A traditional braking assembly typically includes a lever portion and damping plates. The lever portion includes connecting columns, and the damping plates each include an arc-shaped groove. When the lever portion rotates, the connecting columns are each driven to move in the arc-shaped groove from the end of the arc-shaped groove farthest from the axis of a guide rail in an initial state to the end of the arc-shaped groove closest to the axis of the guide rail in the initial state, which in turn drives the damping plates to move close to each other to clamp the knob device, thereby realizing the braking. However, this braking method has a complex structure and is more expensive and inconvenient to assemble. Moreover, during the braking process, the braking force is transmitted indirectly through the cooperation between the connecting column and the arc-shaped groove, resulting in a poor braking effect.

Figure 1:
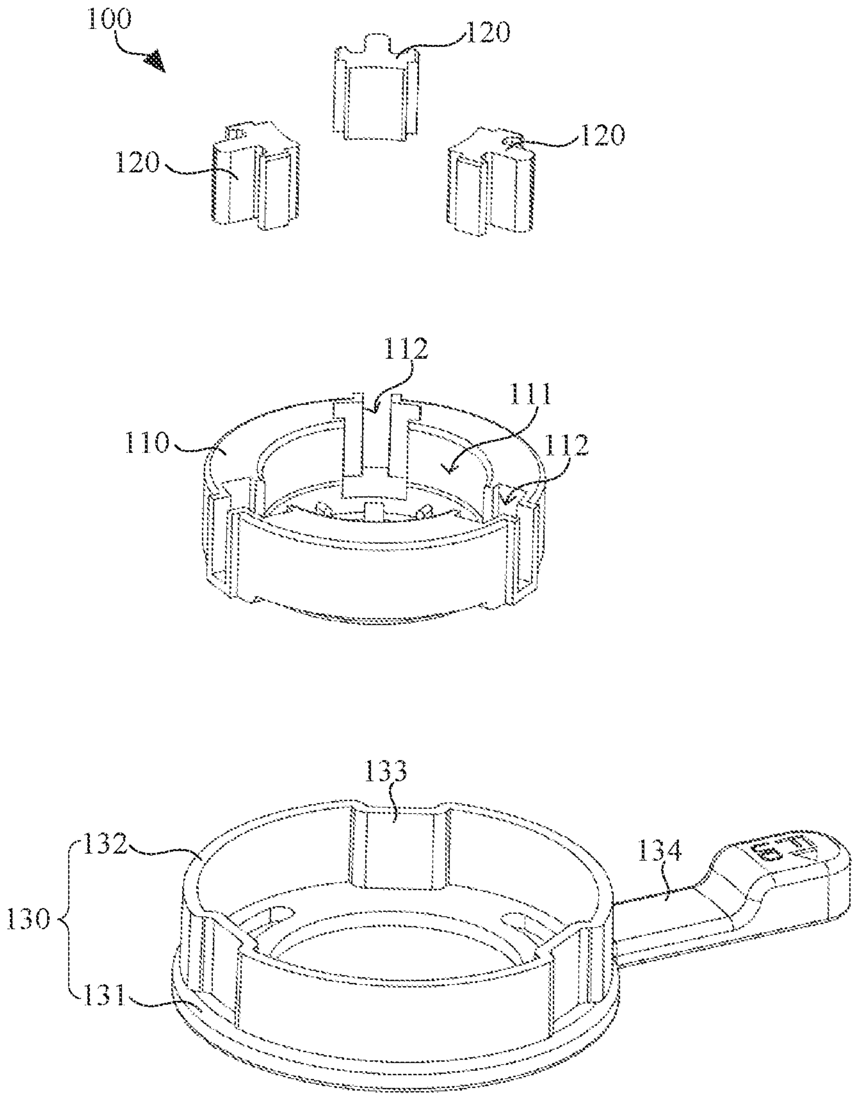
FIG. 1 is an exploded perspective view showing a structure of an endoscope knob brake device according to an embodiment.
Figure 6:
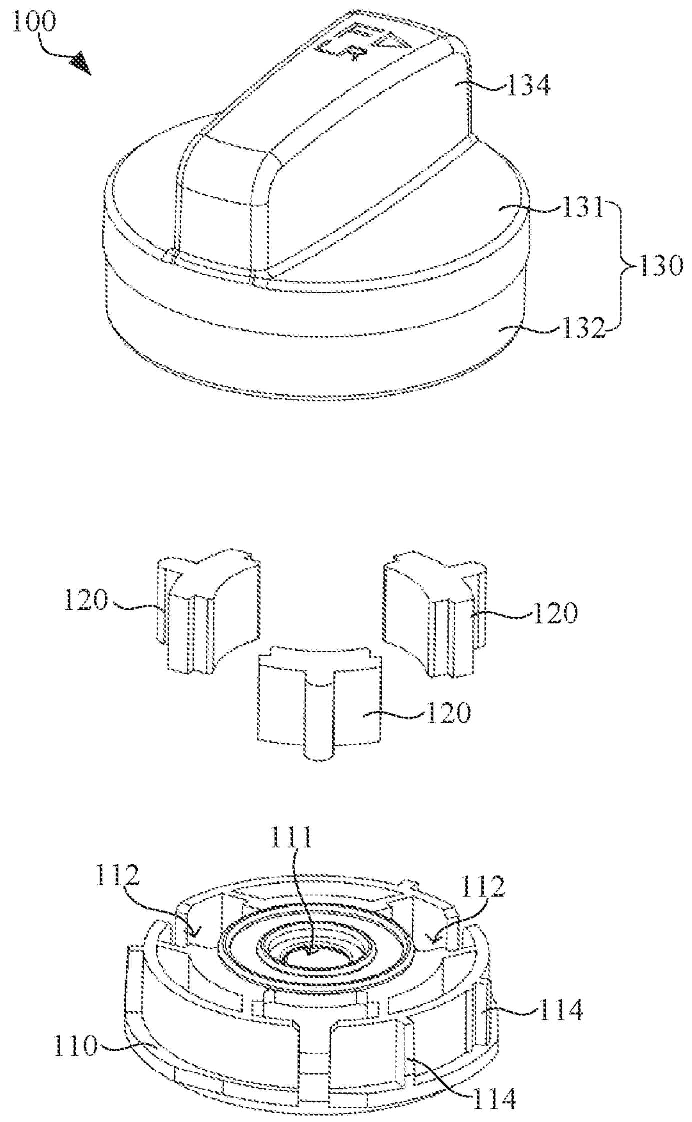
FIG. 6 is another exploded perspective view showing the structure of the endoscope knob brake device according to another embodiment.

In an embodiment, referring to FIG. 1 and FIG. 6, an endoscope knob brake device 100 is provided. The endoscope knob brake device 100 includes a fixed frame 110, a brake member 120, and a brake knob 130. The fixed frame 110 defines an operating cavity 111, which is configured for a knob mechanism 300 to pass through. At least two sliding grooves 112 are defined at intervals and surround the operating cavity 111 on the fixed frame 110. One end of each sliding groove 112 is in communication with the operating cavity 111, and the other end is configured to communicate with the outside of the fixed frame 110. There are at least two brake members 120. Each brake member 120 is slidably installed in the corresponding sliding groove 112 in a one-to-one correspondence, and the brake member 120 passes through the sliding groove 112 and extends out of the fixed frame 110. The brake knob 130 is sleeved over the fixed frame 110. At least two spaced-apart pushing portions 133 are arranged on the inner wall of the brake knob 130. When the brake knob 130 is rotated to a preset angle, the pushing portions 133 push, in a one-to-one correspondence, the brake members 120 to move toward the operating cavity 111 to hold the knob mechanism 300 tightly.

According to the above endoscope knob brake device 100, the brake members 120 are slidably arranged in the sliding grooves 112 in a one-to-one correspondence, and it is ensured that the brake members 120 pass through the sliding grooves 112, respectively, and extend out of the fixed frame 110. When the brake knob 130 sleeved over the fixed frame 110 rotates to the preset angle, each pushing portion 133 on the inner wall of the brake knob 130 contacts the corresponding brake member 120 and pushes the brake member 120 to move in the corresponding sliding groove 112. Since the sliding grooves 112 are in communication with the operating cavity 111, each brake member 120 is pushed by the pushing portion 133 to insert into the operating cavity 111 and finally hold the knob mechanism 300 tightly, thus braking the knob mechanism 300. In this way, through the matching structure between the brake members 120 and the brake knob 130, the brake members 120 are directly driven to move in the sliding grooves 112 during the braking process, thereby realizing the braking on the knob mechanism 300. The structural design is ingenious and simple, and the braking force transmission is direct and effective, ensuring a better braking effect on the knob. In addition, during assembly, it is only required to place the brake member 120 slidably in the sliding groove 112, which effectively simplifies the assembly process and facilitates the improvement of assembly efficiency.

It should be noted that the "preset angle" should be understood as follows: when the knob mechanism 300 needs to be braked, after the brake knob 130 rotates a certain angle clockwise or counterclockwise around the rotation axis thereof, the pushing portions 133 on the brake knob 130 push the brake members 120 to move toward the operating cavity 111 within the sliding grooves 112. The angle may be any angle value from 0° (excluding 0°) to 360° (excluding 360°).

It should also be noted that when the knob mechanism 300 inserts into the operating cavity 111, the knob mechanism 300 may pass through the brake knob 130. Alternatively, the knob mechanism 300 may not pass through the brake knob 130, i.e., the brake knob 130 covers the knob mechanism 300. In addition, one end of the brake member 120 facing the operating cavity should be designed to be able to fit the outer contour of the knob mechanism 300, so that it can restrict the knob mechanism 300 from continuing to rotate when the at least two brake members 120 hold the knob mechanism 300 tightly. It should be understood that, in order to improve the holding effect, an anti-skid structure can be provided at one end of the brake member 120 facing the operating cavity, such as adding anti-skid teeth, anti-skid patterns, anti-skid damping layers, etc.

Figure 3:
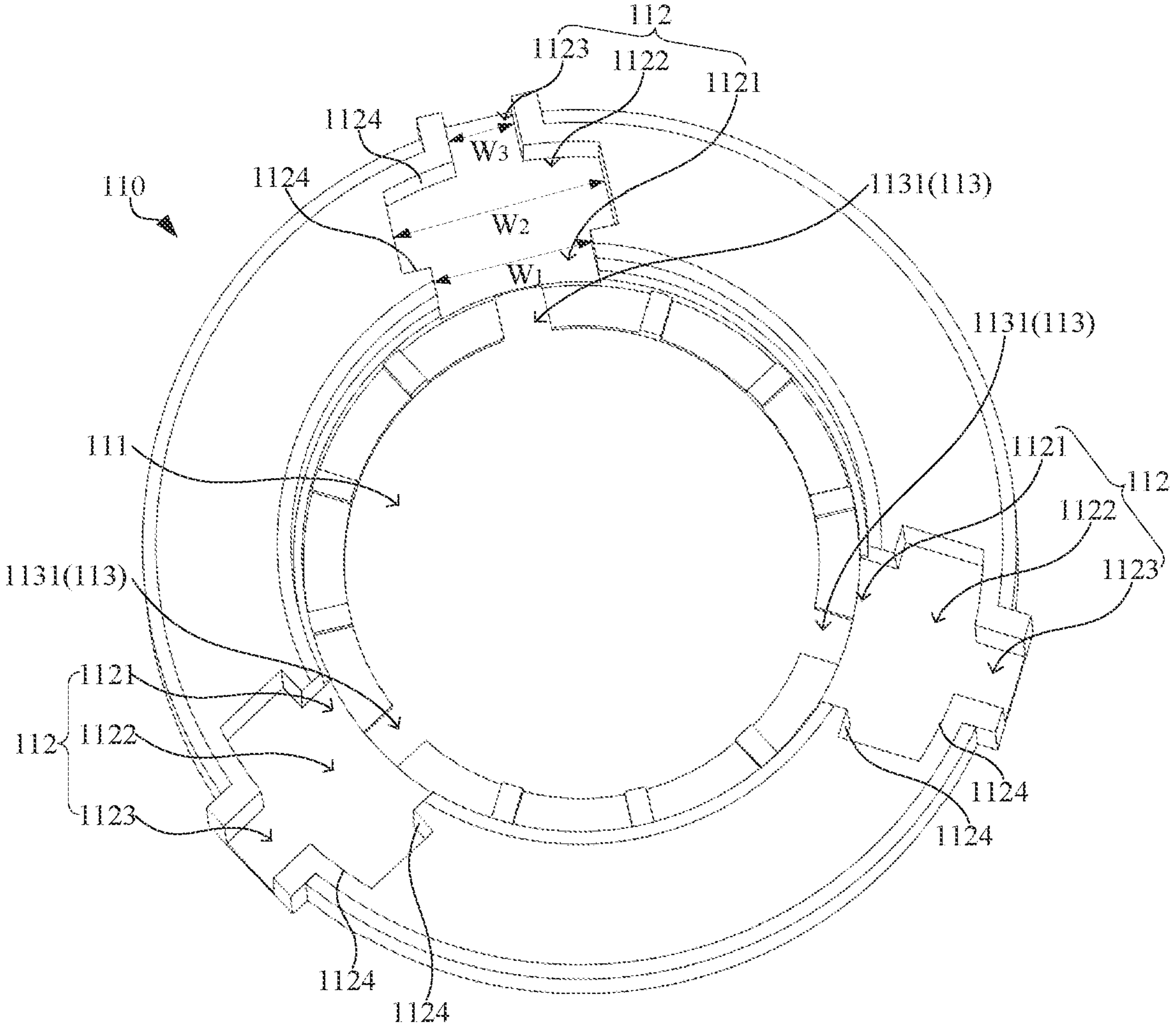
FIG. 3 is a schematic structural view of a fixed frame according to an embodiment.

Further, referring to FIG. 3, the sliding groove 112 includes a first groove section 1121, a second groove section 1122, and a third groove section 1123 that are communicated in sequence. The first groove section 1121 is in communication with the operating cavity 111. The third groove section 1123 is configured to be in communication with the outside of the fixed frame 110. The brake member 120 is slidably installed in the second groove section 1122, one end of the brake member 120 extends into the first groove section 1121, and the other end of the brake member 120 passes through the third groove section 1123 and extends out of the fixed frame 110. In this embodiment, the sliding groove 112 is designed as a three-section structure. Before braking, one end of the brake member 120 passes through the third groove section 1123 and extends out of the fixed frame 110. During braking, under the action of the pushing portion 133, the other end of the brake member 120 inserts into the operating cavity 111 through the first groove section 1121 to hold the knob mechanism 300 tightly.

Figure 4:
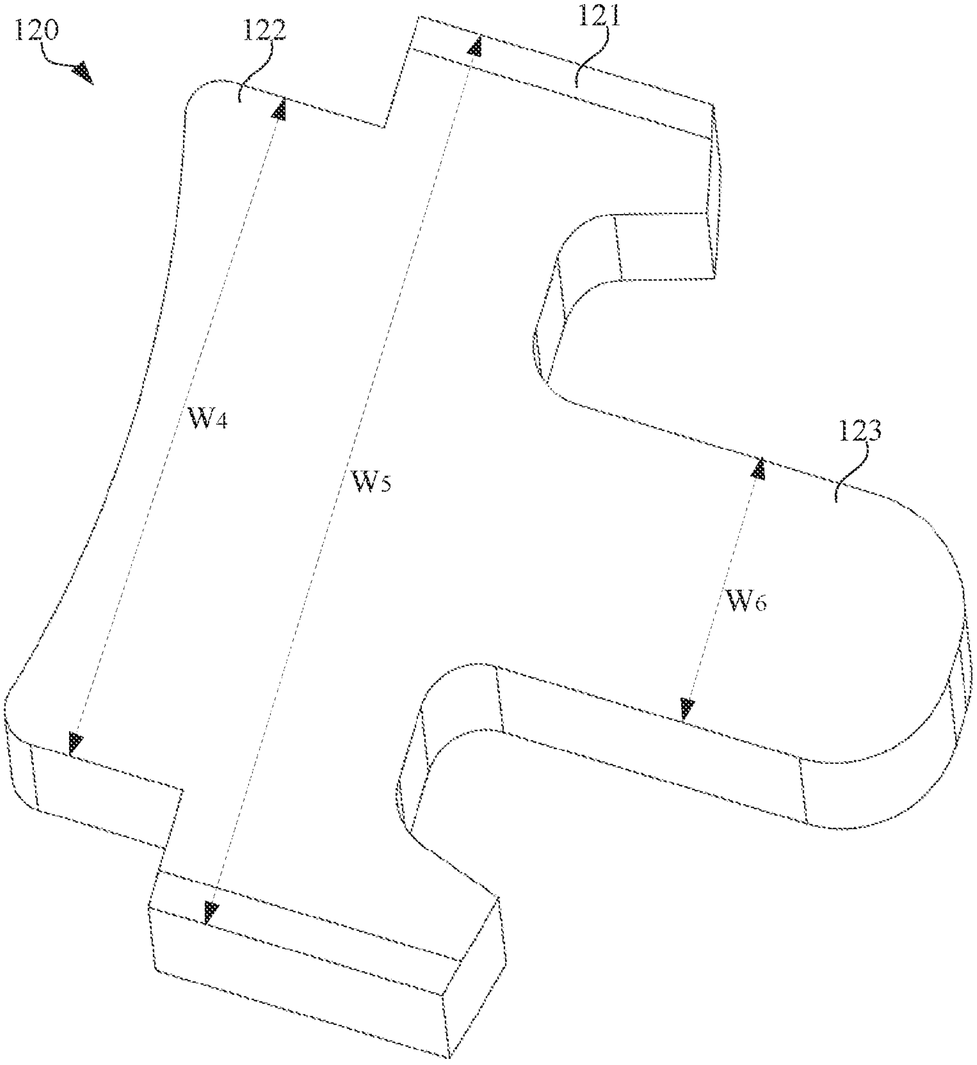
FIG. 4 is a schematic structural view of a brake member according to an embodiment.

Furthermore, referring to FIG. 4, the brake member 120 includes a main body 121, a holding portion 122, and a transmission portion 123. The holding portion 122 and the transmission portion 123 are respectively arranged at opposite ends of the main body 121. The holding portion 122 is located in the first groove section 1121. The transmission portion 123 is located in the third groove section 1123 and partially extends out of the fixed frame 110. Limiting walls 1124 are formed between the first groove section 1121 and the second groove section 1122, and between the second groove section 1122 and the third groove section 1123, respectively. The main body 121 is slidably disposed in the second groove section 1122, and is respectively limited by the limiting walls 1124 between the first groove section 1121 and the second groove section 1122, and the limiting walls 1124 between the second groove section 1122 and the third groove section 1123. In the limiting arrangement, when the main body 121 is in coordination with the limiting walls 1124 adjacent to the third groove section 1123, a part of the transmission portion 123 passes through the third groove section 1123 and extends out of the fixed frame 110. When the main body 121 is in coordination with the limiting walls 1124 adjacent to the first groove section 1121, the holding portion 122 passes through the first groove section 1121 and extends into the operating cavity 111. In this way, the movement range of the main body 121 within the second groove section 1122 is limited by the limiting walls 1124 between the first groove section 1121 and the second groove section 1122 and the limiting walls 1124 between the second groove section 1122 and the third groove section 1123, so as to prevent the brake member 120 from slipping out of the sliding groove 112, which causes the endoscope knob brake device 100 to be ineffective, realizing effective braking.

Optionally, the holding portion 122 and the transmission portion 123 may be connected to the main body 121 through, but are not limited to, a bolt connection, threaded sleeve connection, clamping connection, welding, riveting, pin connection, integrated molding, etc. The integrated molding should be understood as follows: injection molding method, extrusion molding method, die-casting method, etc.

Figure 8:
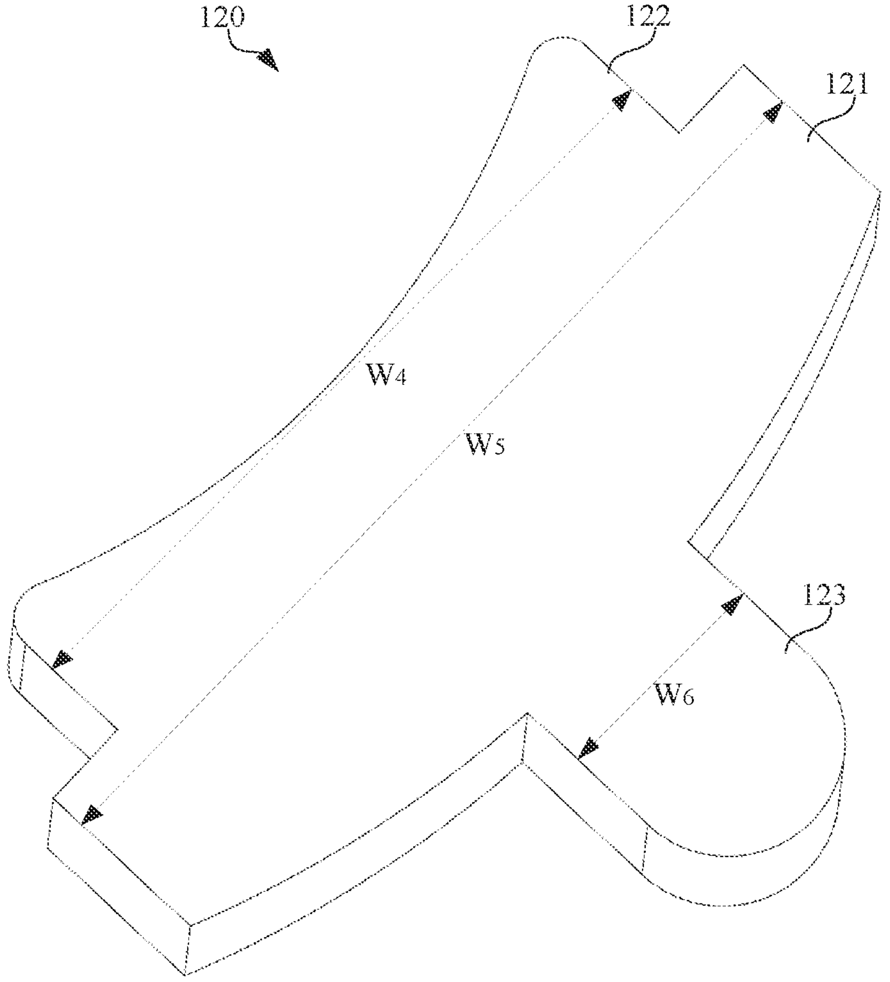
FIG. 8 is a schematic structural view of a brake member according to another embodiment.

Specifically, referring to FIG. 4 and FIG. 8, the transmission portion 123, the main body 121, and the holding portion 122 are integrated, which is not only beneficial to simplifying the manufacturing process but also beneficial to ensuring the structural stability of the brake member 120.

It should be understood that the brake member 120 is an integrated structure, its shape can be designed with various options, such as an "m" shape, etc. The shape of the brake member 102 is not limited in this embodiment.

In an embodiment, referring to FIG. 3, the width $W_1$ of the first groove section 1121 and the width $W_3$ of the third groove section 1123 are both smaller than the width $W_2$ of the second groove section 1122, so that the first groove section 1121 and the third groove section 1123 respectively form the limiting walls 1124 with the second groove section 1122. The width $W_4$ of the holding portion 122 and the width $W_6$ of the transmission portion 123 are both smaller than the width $W_5$ of the main body 121. It can be seen that during the braking process, by utilizing the limiting walls 1124 formed on both sides of the second groove section 1122 by the width difference between the second groove section 1122 and the first groove section 1121 and the width difference between the second groove section 1122 and the third groove section 1123, the main body 121 is stably limited to move back and forth within the second groove section 1122, ensuring a more stable braking structure.

It should be noted that the first groove section 1121 is located in the middle of the second groove section 1122. Two limiting walls 1124 can be formed by the width difference between the first groove section 1121 and the second groove section 1122. Alternatively, one limiting wall 1124 can also be formed if the first groove section 1121 is not located in the middle of the second groove section 1122. Similarly, the third groove section 1123 is located in the middle of the second groove section 1122. Two limiting walls 1124 can be formed by the width difference between the third groove section 1123 and the second groove section 1122. Alternatively, one limiting wall 1124 can also be formed if the third groove section 1123 is not located in the middle of the second groove section 1122.

Figure 5:
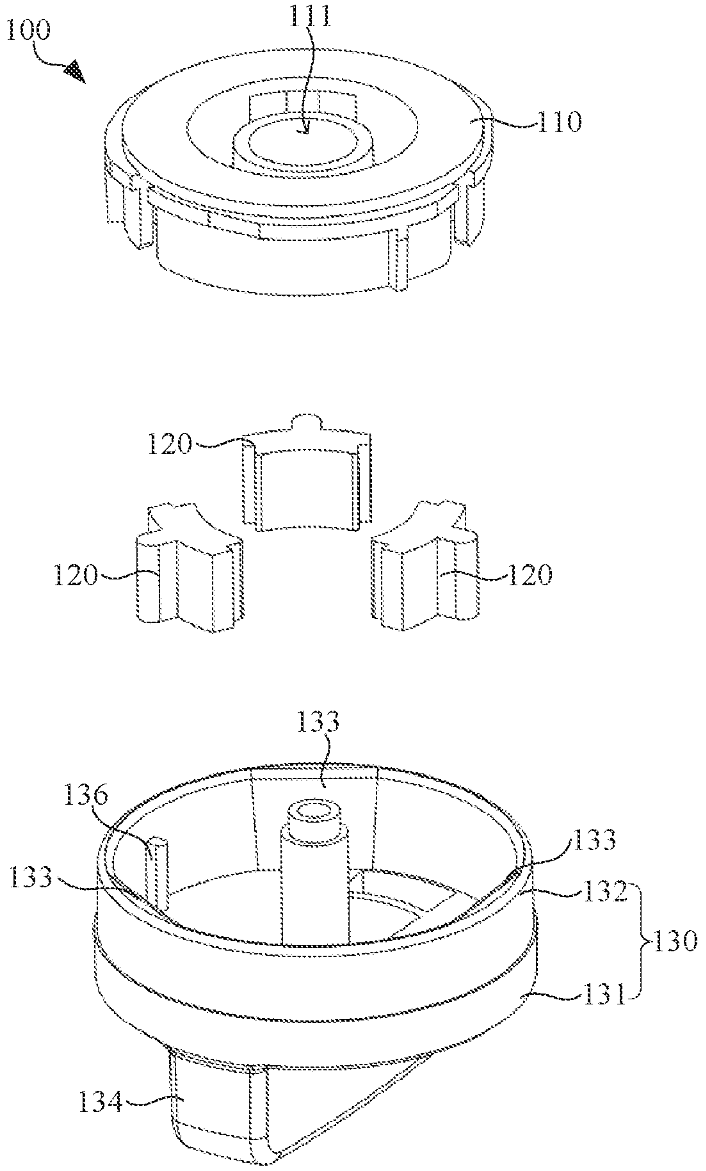
FIG. 5 is an exploded perspective view showing a structure of an endoscope knob brake device according to another embodiment.

In an embodiment, referring to FIG. 1 and FIG. 5, the brake knob 130 includes a knob body 131 and an annular sleeve 132 arranged on the knob body 131. The annular sleeve 132 is sleeved over the fixed frame 110, and the pushing portions 133 are arranged on the inner wall of the annular sleeve 132. In this way, when the annular sleeve 132 is driven to rotate outside the fixed frame 110, the pushing portions 133 on the inner wall thereof each contact the extended portion of the corresponding brake member 120 and push the brake member 120 to move.

Optionally, the pushing portions 133 may be connected to the annular sleeve 132 through, but are not limited to, a bolt connection, threaded sleeve connection, clamping connection, welding, riveting, pin connection, integrated molding, etc.

It should be noted that the knob body 131 may include a through hole for the knob mechanism 300 to pass through to facilitate assembly.

Further, referring to FIG. 1 and FIG. 5, the pushing portions 133 are formed by the inner wall of the annular sleeve 132 protruding toward the center of the annular sleeve 132, i.e., the pushing portions 133 and the annular sleeve 132 are integrated, which makes it more convenient to manufacture.

Specifically, referring to FIG. 1 and FIG. 5, the number of the pushing portions 133, the brake members 120, and the sliding grooves 112 are all three. The three sliding grooves 112 are arranged at intervals around the circumference of the operating cavity 111. The three pushing portions 133 are arranged at intervals along the circumferential direction of the annular sleeve 132.

Figure 2:
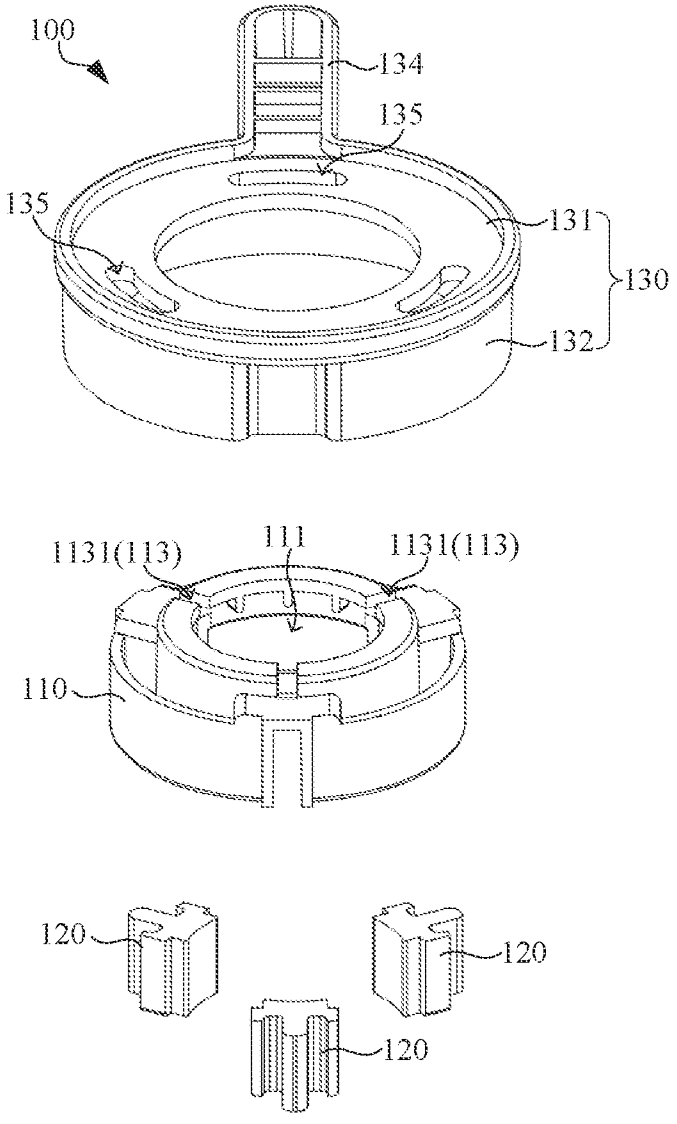
FIG. 2 is another exploded perspective view showing the structure of the endoscope knob brake device according to an embodiment.

In an embodiment, referring to FIG. 2 and FIG. 6, the brake knob 130 includes an toggle portion 134. The toggle portion 134 protrudes and extends along the radial direction of the brake knob 130. Alternatively, the toggle portion 134 protrudes and extends in a direction away from the fixed frame 110. It can be seen that this embodiment provides two different structures of the toggle portion 134. By designing different toggle portions 134, it is convenient for the operator to drive the brake knob 130 to rotate, thereby improving the operability of the product.

Figure 7:
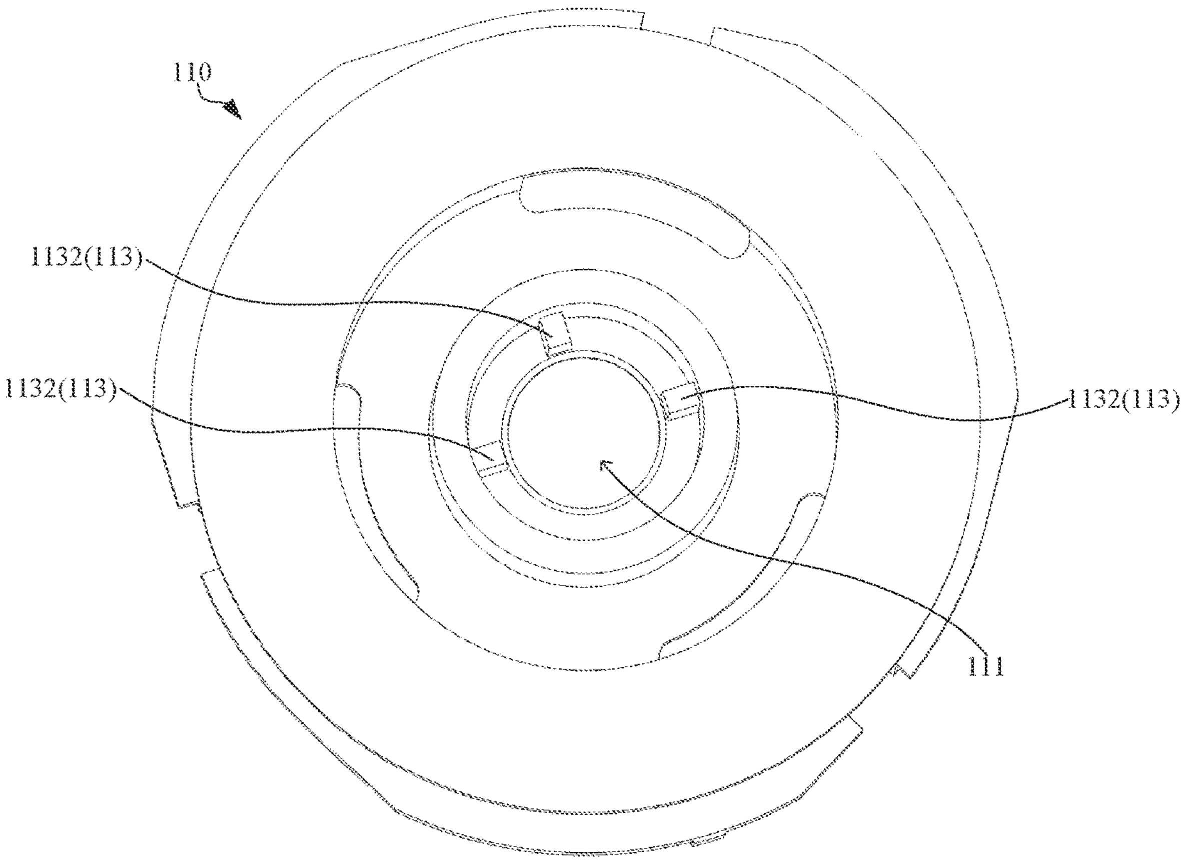
FIG. 7 is a schematic structural view of a fixed frame according to another embodiment.
Figure 9:
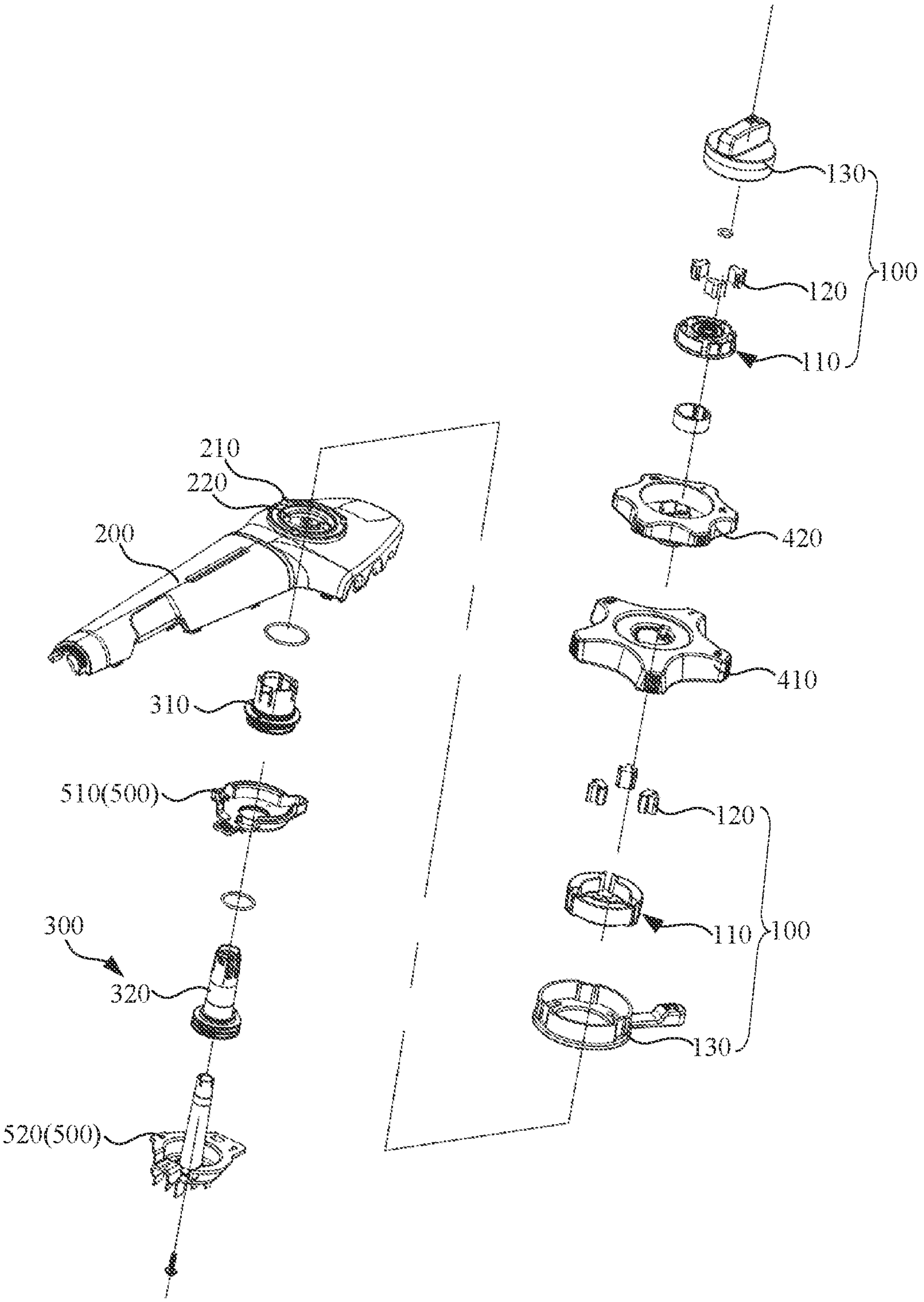
FIG. 9 is an exploded schematic view showing a structure of an endoscope handle according to an embodiment.

In an embodiment, referring to FIG. 2 and FIG. 7, the fixed frame 110 includes a first positioning portion 113, which is configured to positionally cooperate with a second positioning portion 220 (as shown in FIG. 9) on the knob mechanism 300 to limit the fixed frame 110, so that the fixed frame rotates with the knob mechanism 300. In this way, through the cooperation of the first positioning portion 113 and the second positioning portion 220, the fixed frame 110 is kept in a relatively fixed state with respect to the knob mechanism 300, so that the brake members 120 hold the knob mechanism 300 tightly.

Optionally, the first positioning portion 113 is a convex structure, and the second positioning portion 220 is a hole or groove. Alternatively, the first positioning portion 113 is a hole or groove, and the second positioning portion 220 is a convex structure.

Further, referring to FIG. 2 and FIG. 7, the first positioning portion 113 is a positioning groove 1131 or a positioning protrusion 1132 on the fixed frame 110.

Specifically, referring to FIG. 9, an endoscope handle includes two endoscope knob brake devices 100. The first positioning portion 113 on one fixed bracket 110 is a positioning groove 1131, which is positionally matched with a second positioning portion 220 on a housing 200 of the knob mechanism 300. The first positioning portion 113 on the other fixed frame 110 is a positioning protrusion 1132, which is positionally matched with a second positioning portion (not shown) on a cable pulley bracket 500.

Furthermore, referring to FIG. 2 and FIG. 7, there are a plurality of first positioning portions 113. The plurality of first positioning portions 113 are arranged at intervals around the operating cavity 111. In this way, the plurality of first positioning portions 113 cooperate with a plurality of second positioning portions 220, so that the rotational limitation of the fixed frame 110 is more effective.

In an embodiment, referring to FIG. 2, the brake knob 130 includes arc-shaped grooves 135. The arc-shaped grooves 135 are arranged around the operating cavity 111. The arc-shaped grooves 135 are configured to cooperate with limiting columns 210 (as shown in FIG. 9) on the housing 200 to limit the rotation range of the brake knob 130. Alternatively, as shown in FIG. 5 and FIG. 6, a first limiting block 136 is disposed on the inner wall of the brake knob 130, and second limiting blocks 114 are disposed on the outer wall of the fixed frame 110. The first limiting block 136 cooperates with the second limiting blocks 114 to limit the rotation range of the brake knob 130. In this way, by means of the arc-shaped grooves 135 or the first limiting block 136, the rotation range of the brake knob 130 is effectively limited, avoiding over-rotation that may lead to structural instability.

In an embodiment, referring to FIG. 9, an endoscope handle is provided. The endoscope handle includes a knob mechanism 300 and at least two endoscope knob brake devices 100 in any one of the above embodiments. The knob mechanism 300 includes a housing 200, a first cable pulley 310, a second cable pulley 320, a first knob 410, and a second knob 420. The first cable pulley 310 extends out of the housing 200 and is connected to the first knob 410. The second cable pulley 320 passes through the first cable pulley 310 and extends out of the housing 200, and is connected to the second knob 420. One endoscope knob brake device 100 is configured to brake the first knob 410, and the other endoscope knob brake device 100 is configured to brake the second knob 420.

In the above-mentioned endoscope handle, the above endoscope knob brake devices 100 are employed. The brake members 120 are slidably arranged in the sliding grooves 112 in a one-to-one correspondence, and it is ensured that brake members 120 pass through the sliding grooves 112, respectively, and extend out of the fixed frame 110. When the brake knob 130 sleeved over the fixed frame 110 rotates to a preset angle, each pushing portion 133 on the inner wall of the brake knob 130 contacts the corresponding brake member 120 and pushes the brake member 120 to move in the corresponding sliding groove 112. Since the sliding grooves 112 are in communication with the operating cavity 111, each brake member 120 is pushed by the pushing portion 133 to insert into the operating cavity 111 and finally hold the knob mechanism 300 tightly, thus braking the knob mechanism 300. In this way, through the matching structure between the brake members 120 and the brake knob 130, the brake members 120 are directly driven to move in the sliding grooves 112, respectively, during the braking process, thereby realizing the braking on the knob mechanism 300. The structural design is ingenious and simple, and the braking force is transmitted directly and effectively, ensuring a better braking effect on the knob. In addition, during assembly, it is only required to place the brake member 120 slidably in the sliding groove 112, which effectively simplifies the assembly process and facilitates the improvement of assembly efficiency.

Further, the knob mechanism 300 further includes a first cable pulley bracket 510 and a second cable pulley bracket 520. The first cable pulley bracket 510 is sleeved on the second cable pulley 320 and covers the first cable pulley 310. The second cable pulley bracket 520 covers the second cable pulley 320, and extends out of the housing 200 through the second cable pulley 320.

In an embodiment, referring to FIG. 9, an endoscope including the endoscope handle in the above embodiments is provided.

According to the above-mentioned endoscope, the above-mentioned endoscope handle is employed. The brake members 120 are slidably arranged in the sliding grooves 112 in a one-to-one correspondence, and it is ensured that the brake members 120 pass through the sliding grooves 112, respectively, and extend out of the fixed frame 110. When the brake knob 130 sleeved over the fixed frame 110 rotates to a preset angle, each pushing portion 133 on the inner wall of the brake knob 130 contacts the corresponding brake member 120 and pushes the brake member 120 to move in the sliding groove 112. Since the sliding grooves 112 are in communication with the operating cavity 111, each brake member 120 is pushed by the pushing portion to insert into the operating cavity 111 and finally holds the knob mechanism 300 tightly, thus braking the knob mechanism 300. In this way, through the matching structure between the brake members 120 and the brake knob 130, the brake members 120 are directly driven to move in the sliding grooves 112, respectively, during the braking process, thereby realizing the braking on the knob mechanism 300. The structural design is ingenious and simple, and the braking force is transmitted directly and effectively, ensuring a better braking effect on the knob. In addition, during assembly, it is only required to place the brake member 120 slidably in the sliding groove 112, which effectively simplifies the assembly process and facilitates the improvement of assembly efficiency.

The technical features in the above embodiments may be randomly combined. For brevity, not all possible combinations of the technical features in the above embodiments are described. However, all the combinations of the technical features should be considered to be included within the scope of the present disclosure, as long as the combinations are not contradictory.

The above-mentioned embodiments only illustrate several embodiments of the present disclosure, and the descriptions of which are relatively specific and detailed, but should not be construed as limitations to the scope of the present disclosure. It should be noted that, for those skilled in the art, variations and improvements can be made without departing from the concept of the present disclosure, which all belong to the protection scope of the present disclosure. Therefore, the protection scope of the present disclosure shall be subject to the appended claims.

In the description of the present disclosure, it should be understood that the orientation or positional relationships indicated by the terms "center", "longitudinal", "transverse", "length", "width", "thickness", "above", "below", "front", "back", "left", "right", "vertical", "horizontal", "top", "bottom", "inside", "outside", "clockwise", "counterclockwise", "axial", "radial direction", "circumferential direction", etc. are based on the orientation or positional relationships shown in the figures, and are merely for the purpose of facilitating the description of the present disclosure and simplifying the description, and do not indicate or imply the device or component referred to must have a specific orientation or must be constructed and operate in a specific orientation, and therefore should not be construed as a limitation of the present disclosure.

In addition, the terms "first" and "second" are used merely for the purpose of description, and should not be construed as indicating or implying relative importance or implicitly indicating a quantity of indicated technical features. Therefore, features defined by "first" or "second" may explicitly or implicitly include at least one of such features. In description of this application, "a plurality of" means at least two, such as two and three unless it is specifically defined otherwise.

In the present disclosure, unless otherwise clearly stated and limited, the terms "installed", "connected", "communicated", "fixed", etc. should be interpreted broadly. For example, it may be a fixed connection, a detachable connection, or integrated. It may also be a mechanical connection or an electrical connection. It may be a direct connection or an indirect connection through an intermediate medium. It may also be an internal connection between two elements or an interactive relationship between two elements, unless otherwise specified limitations. For those of ordinary skill in the art, the specific meanings of the above terms in the present disclosure can be understood according to specific situations.

In the present disclosure, unless otherwise expressly stated and limited, a first feature being "on" or "below" a second feature may refer to a direct connection between the first feature and the second feature or an indirect connection between the first feature and the second feature through an intermediate medium. Furthermore, the first feature being "on", "above" and "over" the second feature may be that the first feature is directly above or diagonally above the second feature, or simply that the first feature is horizontally higher than the second feature. The first feature being "under", "below" and "beneath" the second feature may be that the first feature is directly below or diagonally below the second feature, or simply that the first feature has a smaller horizontal height than the second feature.

It should be noted that when an element is referred to as being "fixed to" or "arranged on" another element, it may be directly on the other element or connected to the other element through intervening elements. When an element is referred to as being "connected" to another element, it may be directly connected to the other element or there may also be intervening elements. The terms "vertical", "horizontal", "above", "below", "left", "right", and similar expressions used herein are merely for illustrative purposes and do not imply the only implementation manner.

What is claimed is:

1. An endoscope knob brake device, comprising:

a fixed frame defining an operating cavity configured for a knob mechanism to pass through, the fixed frame comprising at least two sliding grooves arranged at intervals around the operating cavity, one end of each sliding groove being in communication with the operating cavity, and the other end of each sliding groove being configured to communicate with an outside of the fixed frame;

at least two brake members being slidably installed in the at least two sliding grooves in a one-to-one correspondence, each brake member passing through the corresponding sliding groove and extends out of the fixed frame; and a brake knob sleeved over the fixed frame, at least two pushing portions are disposed at intervals on an inner wall of the brake knob, wherein when the brake knob is rotated to a preset angle, the pushing portions push, in a one-to-one correspondence, the brake members to move toward the operating cavity, thereby holding the knob mechanism;

wherein each sliding groove comprises a first groove section, a second groove section, and a third groove section that are communicated in sequence, the first groove section is communicated with the operating cavity, the third groove section is configured to communicate with the outside of the fixed frame, the brake member is slidably installed in the second groove section, one end of the brake member extends into the first groove section, and the other end of the brake member passes through the third groove section and extends out of the fixed frame;

wherein each brake member comprises a main body, a holding portion, and a transmission portion, the holding portion and the transmission portion are respectively arranged at opposite ends of the main body, the holding portion is located in the first groove section, the transmission portion is located in the third groove section and partially extends out of the fixed frame, limiting walls are formed between the first groove section and the second groove section, and between the second groove section and the third groove section, respectively, the main body is slidably installed in the second groove section and is limited by the limiting wall between the first groove section and the second groove and the limiting wall between the second groove section and the third groove section; and wherein a width $W_1$ of the first groove section and a width $W_3$ of the third groove section are both smaller than a width $W_2$ of the second groove section, such that the limiting walls are formed between the first groove section and the second groove section, and between the third groove section and the second groove section, respectively, and a width $W_4$ of the holding portion and a width $W_6$ of the transmission portion are both smaller than a width $W_5$ of the main body.

2. The endoscope knob brake device according to claim 1, wherein the brake knob comprises a knob body and an annular sleeve arranged on the knob body, the annular sleeve is sleeved over the fixed frame, and the pushing portions are arranged on an inner wall of the annular sleeve.

3. The endoscope knob brake device according to claim 2, wherein the pushing portions are formed by the inner wall of the annular sleeve protruding toward a center of the annular sleeve.

4. The endoscope knob brake device according to claim 1, wherein the brake knob comprises a toggle portion protruding and extending along a radial direction of the brake knob; or the brake knob comprises a toggle portion protruding and extending in a direction away from the fixed frame.

5. The endoscope knob brake device according to claim 1, wherein the fixed frame comprises a first positioning portion configured to positionally cooperate with a second positioning portion on the knob mechanism to limit the fixed frame such that the fixed frame rotates with the knob mechanism.

6. The endoscope knob brake device according to claim 5, wherein the first positioning portion is a positioning groove or a positioning protrusion on the fixed frame.

7. The endoscope knob brake device according to claim 5, wherein a plurality of the first positioning portions are configured, and the plurality of the first positioning portions are arranged at intervals around the operating cavity.

8. The endoscope knob brake device according to claim 1, wherein the brake knob comprises arc-shaped grooves arranged around the operating cavity, and the arc-shaped grooves are configured to cooperate with limiting columns on a housing of the knob mechanism to limit a rotation range of the brake knob; or a first limiting block is disposed on an inner wall of the brake knob, second limiting blocks are disposed on an outer wall of the fixed frame, and the first limiting block cooperates with the second limiting blocks to limit the rotation range of the brake knob.

9. An endoscope handle, wherein the endoscope handle comprises a knob mechanism and two endoscope knob brake devices, wherein each of the two endoscope knob brake devices comprises:

a fixed frame defining an operating cavity configured for a knob mechanism to pass through, the fixed frame comprising at least two sliding grooves arranged at intervals around the operating cavity, one end of each sliding groove being in communication with the operating cavity, and the other end of each sliding groove being configured to communicate with an outside of the fixed frame;

at least two brake members being slidably installed in the at least two sliding grooves in a one-to-one correspondence, each brake member passing through the corresponding sliding groove and extends out of the fixed frame; and a brake knob sleeved over the fixed frame, at least two pushing portions are disposed at intervals on an inner wall of the brake knob, wherein when the brake knob is rotated to a preset angle, the pushing portions push, in a one-to-one correspondence, the brake members to move toward the operating cavity, thereby holding the knob mechanism, and wherein each sliding groove comprises a first groove section, a second groove section, and a third groove section that are communicated in sequence, the first groove section is communicated with the operating cavity, the third groove section is configured to communicate with the outside of the fixed frame, the brake member is slidably installed in the second groove section, one end of the brake member extends into the first groove section, and the other end of the brake member passes through the third groove section and extends out of the fixed frame;

each brake member comprises a main body, a holding portion, and a transmission portion, the holding portion and the transmission portion are respectively arranged at opposite ends of the main body, the holding portion is located in the first groove section, the transmission portion is located in the third groove section and partially extends out of the fixed frame, limiting walls are formed between the first groove section and the second groove section, and between the second groove section and the third groove section, respectively, the main body is slidably installed in the second groove section and is limited by the limiting wall between the first groove section and the second groove and the limiting wall between the second groove section and the third groove section; and a width $W_1$ of the first groove section and a width $W_3$ of the third groove section are both smaller than a width $W_2$ of the second groove section, such that the limiting walls are formed between the first groove section and the second groove section, and between the third groove section and the second groove section, respectively, and a width $W_4$ of the holding portion and a width $W_6$ of the transmission portion are both smaller than a width $W_5$ of the main body; and wherein the knob mechanism comprises a housing, a first cable pulley, a second cable pulley, a first knob, and a second knob, the first cable pulley extends out of the housing and is connected to the first knob, the second cable pulley passes through the first cable pulley, extends out of the housing, and is connected to the second knob, one of the endoscope knob brake devices is configured to brake the first knob or the first cable pulley, and the other one of the endoscope knob brake devices is configured to brake the second knob or the second cable pulley.

10. An endoscope comprising the endoscope handle according to claim 9.

11. The endoscope knob brake device according to claim 1, wherein an anti-skid structure is disposed at an end of each brake member facing the operating cavity.

12. The endoscope knob brake device according to claim 1, wherein an end of each brake member facing the operating cavity fits an outer contour of the knob mechanism.

13. The endoscope knob brake device according to claim 1, the transmission portion, the main body, and the holding portion are integrated.

14. The endoscope handle according to claim 9, wherein the brake knob comprises a knob body and an annular sleeve arranged on the knob body, the annular sleeve is sleeved over the fixed frame, and the pushing portions are arranged on an inner wall of the annular sleeve.

* * * * *